United States Patent [19]

Löhn

[11] Patent Number: 5,082,443
[45] Date of Patent: * Jan. 21, 1992

[54] DENTAL SPRAY HANDPIECE

[75] Inventor: Gerd Löhn, Biberach/Rissegg, Fed. Rep. of Germany

[73] Assignee: Kaltenbach & Voight GmbH & Co., Biberach an der Riss, Fed. Rep. of Germany

[*] Notice: The portion of the term of this patent subsequent to Dec. 12, 2006 has been disclaimed.

[21] Appl. No.: 614,011

[22] Filed: Nov. 14, 1990

Related U.S. Application Data

[63] Continuation of Ser. No. 249,790, Sep. 27, 1988, abandoned.

[30] Foreign Application Priority Data

Oct. 14, 1987 [DE] Fed. Rep. of Germany ....... 3734862

[51] Int. Cl.$^5$ ............................................. A61G 17/02
[52] U.S. Cl. ........................................ 433/80; 433/29
[58] Field of Search ................. 433/80, 81, 82, 83, 433/84, 85, 88, 29

[56] References Cited

U.S. PATENT DOCUMENTS

| | | | |
|---|---|---|---|
| 3,478,430 | 11/1969 | Park et al. | 433/80 |
| 4,017,974 | 4/1977 | Sotman et al. | 433/85 |
| 4,108,178 | 8/1978 | Betush | 433/80 X |
| 4,227,878 | 10/1980 | Lohn | 433/80 |
| 4,619,612 | 10/1986 | Weber et al. | 433/80 |
| 4,648,838 | 3/1987 | Schlacter | 433/29 |
| 4,676,749 | 6/1987 | Mabille | 433/88 |
| 4,680,011 | 7/1987 | Boinot | 433/29 |
| 4,790,751 | 12/1988 | Reinhardt et al. | 433/80 X |
| 4,886,455 | 12/1989 | Lohn | 433/29 X |

FOREIGN PATENT DOCUMENTS 1416921 10/1968 Fed. Rep. of Germany .
3337166 4/1985 Fed. Rep. of Germany .

*Primary Examiner*—Robert P. Swiatek
*Assistant Examiner*—Nicholas D. Lucchesi
*Attorney, Agent, or Firm*—Scully, Scott, Murphy & Presser

[57] ABSTRACT

A dental spray handpiece, consisting of a gripping sleeve possessing a connection for media at one end thereof and a media discharge at its other end, and in which sleeve there are arranged media conduits leading from the media connection to the media discharge. A tubular member or cannula for further conducting the media egressing from the media discharge is arranged at the media-discharging end of the gripping sleeve, the cannula including forwarding passageways for the advancing of the media, and which communicate with the surroundings through discharge orifices at the free end of the cannula.

10 Claims, 2 Drawing Sheets

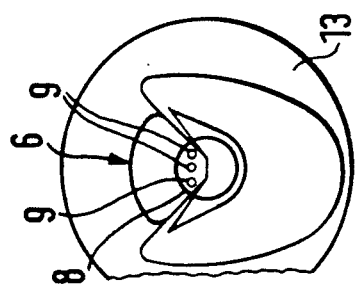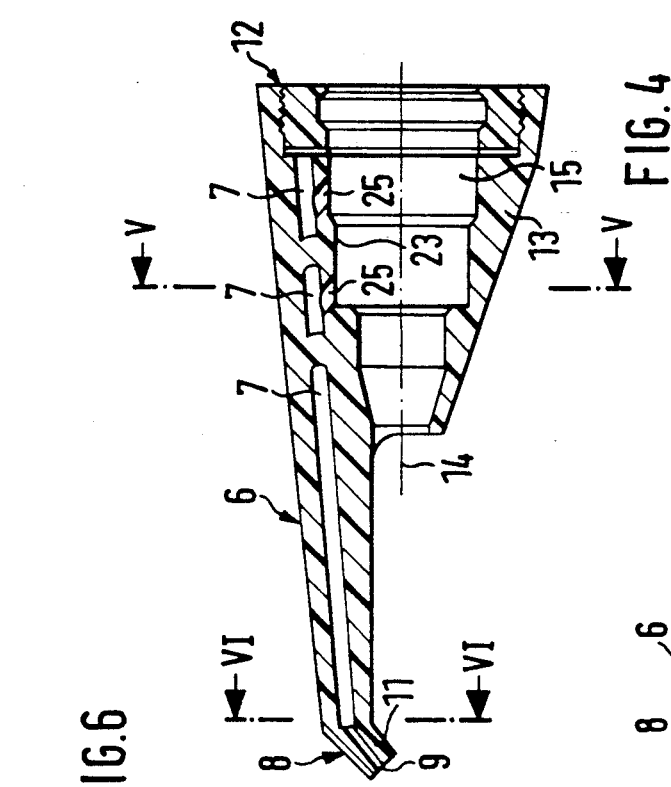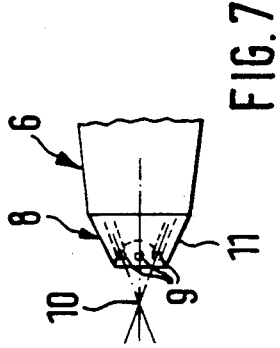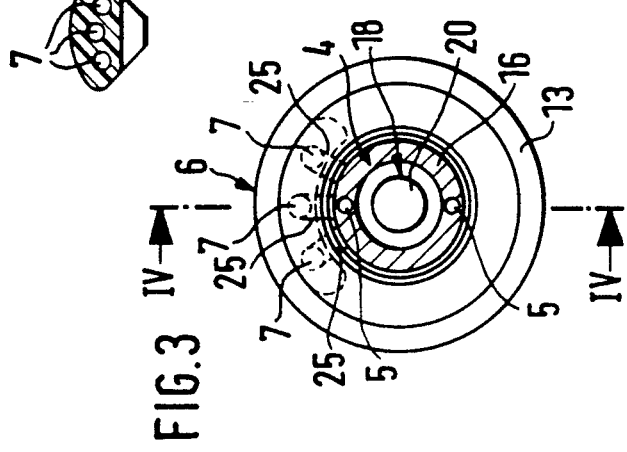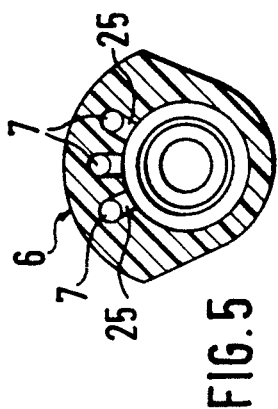

DENTAL SPRAY HANDPIECE

This application is a continuation of application Ser. No. 249,790, filed on Sept. 27, 1988, now abandoned.

BACKGROUND OF THE INVENTION
1. Field of the Invention

The present invention relates to a dental spray handpiece, consisting of a gripping sleeve possessing a connection for media at one end thereof and a media discharge at its other end, and in which sleeve there are arranged media conduits leading from the media connection to the media discharge. A tubular member or cannula for further conducting the media egressing from the media discharge is arranged at the media-discharging end of the gripping sleeve, the cannula including forwarding passageways for the advancing of the media, and which communicate with the surroundings through discharge orifices at the free end of the cannula.

2. Discussion of the Prior Art

A spray handpiece of the type as set forth hereinabove is known from the disclosures of German Laid-open Patent Appln. 33 37 166 and German Laid-Open Patent Appln. 14 16 921. In this known spray handpiece, the forwarding passageways which are arranged in the cannula are concentrically positioned within each other. This has the consequence that the cannula evidences a relatively heavy thickness. Because of the thereby necessitated large cross-sectional dimensions, the treating person has his view obstructed and the manipulation rendered more difficult.

SUMMARY OF THE INVENTION

The invention as set forth herein through a spray handpiece of the type under consideration, and to obviate the disadvantages of the prior art, affords the advantage that the forwarding passageways in the cannula are arranged so as to be located adjacent each other, as a result of which cannula is formed as a flat stem. This allows for the provision of a spray handpiece of the above-mentioned type, in which the cannula has the thinnest possible cross-section.

The advantages which are achieved through the invention can be essentially ascertained in that the cannula provides a thin structural component which, especially in the molar region of the patient, causes the least possible obstruction to the view of the treating personnel, and facilitates for an improved manipulation. Moreover, the flat configuration for the cannula affords for an improved pressing away of soft mouth portions and for a better support; for example, against the jaw.

In essence, in the known dental spray handpiece which is described in German Laid-open Patent Appln. 14 16 921, the discharge orifices of the media-forwarding passageways are located adjacent to each other; however, the forwarding passageways themselves which extend through the cannula are, in this instance, also arranged within each other, such that, also in this case, there is obtained a relatively thick cannula with the above-mentioned attendant disadvantages.

BRIEF DESCRIPTION OF THE DRAWINGS

Reference may now be had to the following detailed description of preferred embodiments of the invention, taken in conjunction with the accompanying drawings; in which:

FIG. 3 illustrates a sectional view taken along line III—III in FIG. 1;

FIG. 4 illustrates a sectional view taken along line IV—IV in FIG. 3, with the omission of the plug connector ascertainable in FIG. 3;

FIG. 5 illustrates a sectional view taken along line V—V in FIG. 4;

FIG. 6 illustrates a sectional view taken along line VI—VI in FIG. 4;

FIG. 7 illustrates, viewed from below, the free end of the cannula shown in FIG. 3; and FIG. 8 illustrates the cannula shown in FIG. 4 in a view towards the free end of the cannula possessing the discharge orifices.

DETAILED DESCRIPTION

Figure 1:
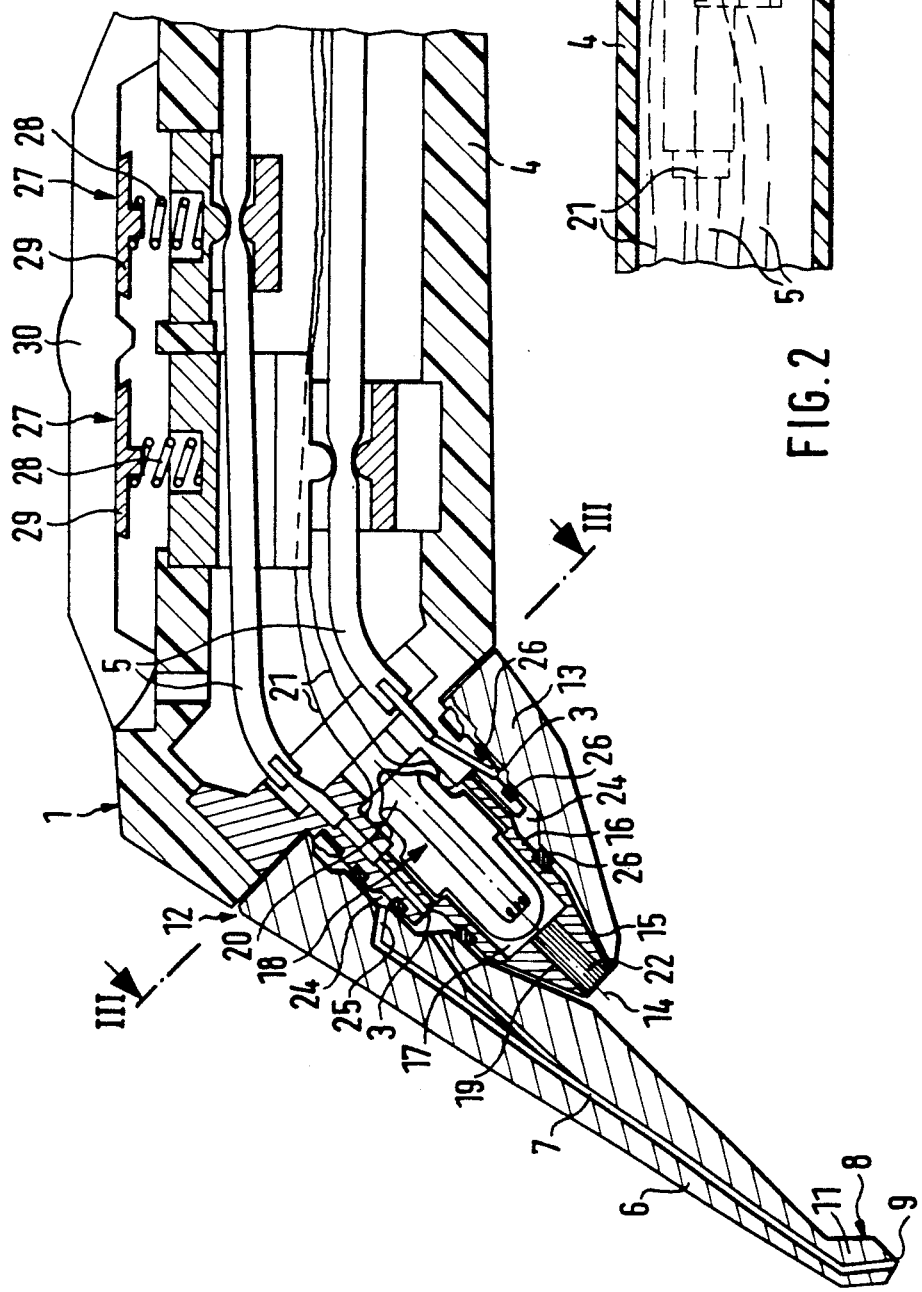
FIG. 1 illustrates a longitudinal sectional view through the end of a spray handpiece at the end thereof towards the discharge of media.
Figure 2:
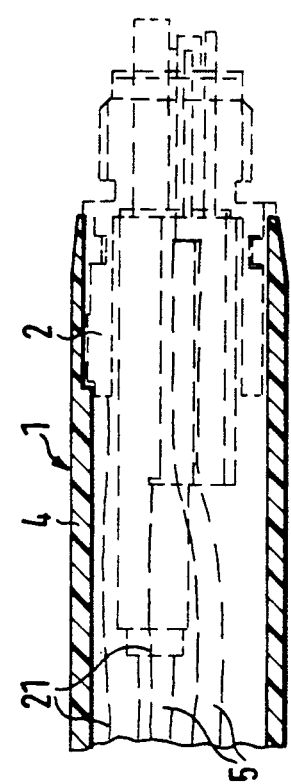
FIG. 2 illustrates, in a reduced scale, a sectional view through the end of the spray handpiece which is distant from the media discharge end shown in FIG. 1.

The illustrated dental spray handpiece 1 is constituted from a gripping sleeve 4 having a media inlet connection 2 at one end thereof, and a media discharge 3 at the other end thereof, in which sleeve there are arranged media conduits 5 leading from the media inlet connection 2 to the media discharge 3. At the media-discharging end of the gripping sleeve 4, there is arranged a tubular member or cannula 6 for the further conductance of media egressing from the media discharge 3, wherein the cannula possesses media-forwarding or advancing passageways 7 for the further advance of the media, which communicate with the surroundings at the free end 8 of the cannula 6 through discharge orifices 9.

The passageways 7 which are arranged within the cannula 6 are located adjacent to each other over essentially the entire length of the cannula; in effect, arranged in practically a single plane, whereby the cannula 6 is formed as a flat stem member.

As illustrated in FIGS. 3 through 8, three media-advancing passageways 7 are provided in the cannula 6. The middle media passageway 7 is formed by a water passageway, whereas the two outer located passageways 7 are, respectively, formed by an air passageway.

As is illustrated in particular by FIG. 7, the discharge orifices 9 of the media-advancing passageways 7 are oriented in such a manner, that the media jets which exit into the surroundings at the free end of the cannula 6 strike at an intersection 10 which is located in front of the free end 8 of the cannula. The discharge orifice 9 of the middle media-advancing passageway 7 is directed straight ahead relative to the free end 8 of the cannula 6, whereas the discharge orifices 9 of the two outer media passageways 7 are directed inwardly towards the axis of the middle discharge orifice 9.

As can be ascertained from FIGS. 1 and 4, the cannula 6 includes an angled or bent end portion 11 at its free end 8 possessing the discharge orifices 9.

A particularly expedient embodiment is obtained with respect to the fastening of thin or flat cannula 6 to the gripping sleeve 4, as illustrated, when the cannula 6 at the end 12 thereof, which is remote from the free end 8, has a lateral thickening piece 13 which is provided with an insert or plug-in opening 15 having the axis 14 thereof directed towards the free end 8 of the cannula, for the detachable mounting thereon of a plug connector 16 projecting from the media-discharging end surface of the gripping sleeve.

The cannula 6 is mounted on the plug connector 16 so as to be rotatable about the axis 14 of the insert opening 15.

As can be ascertained from FIG. 4, the media-advancing passageways of the cannula 6 are slightly inclined relative to the axis of the insert opening 15.

The insert connector 16 possesses a hollow space 17 in its interior for the receipt of a light-emitting element 18, and at the end thereof which is distant from the handpiece, a light-transmissive opening 19 for the light which is emitted by the light-emitting element 18, whereby the insert opening 15 is also open towards the free end 8 of the cannula for the passing-through of the light.

The light-emitting element 18 can be a light-conductor which is powered from a source of light. In the illustrated instance, in accordance with FIG. 1, the light-emitting element 18 is formed by an incandescent lamp or lightbulb 20, for the operation of which there is arranged an electrical supply circuit 21 in the gripping sleeve 4. Arranged within the light-transmissive opening 19 of the plug connector 16 is a light conductor 22; for example, a glass insert.

The plug connector 16 which is plugged into the insert opening 15 of the cannula 6 forms, in conjunction with the wall structure 23 of the insert opening 15, transfer chambers 24 for the transfer of the media from the media discharge 3 of the gripping sleeve 4 to radial conduit sections 25 of the media-advancing passageways 7. The transfer chambers 24 are hereby sealed off through the intermediary of sealing rings which are arranged on the plug connector 16. The sealing rings 26 are constructed in the shape of O-rings.

The gripping sleeve 4 additionally possesses a shutoff valve 27 for, respectively, each of the media conduits 5.

The two shutoff valves 27 are each equipped with a pushbutton 29 which is depressable in opposition to the biasing action of a return spring 28 from the closed position into the open position, whereby the two pushbuttons 29 are covered by an elastic covering 30.

Instead of being angled, as illustrated, the media-discharging end portion of the gripping sleeve 4 can also extend linearly or straight.

What is claimed is:

1. Dental spray handpiece, comprising a gripping sleeve having a media connection at one end thereof and a media discharge at an opposite end; media conduits extending through said sleeve from the media connection to the media discharge; a cannula on the media-discharge end of said gripping sleeve for the further advance of media egressing from the media discharge, said cannula including three passageways arranged therein for the further advance of the media, discharge orifices in communication with the surroundings at the free end of said cannula, said cannula including an angled end portion at the free end of said cannula possessing said discharge orifices, said passageways in the cannula being arranged adjacent each other such that the cannula is formed as a flat stem member, said cannula including a lateral thickened portion at the end remote from the free end thereof, said thickened portion including an insert opening having an axis oriented towards the free end of the cannula for detachable attachment of a plug connector projecting from the media-discharge end surface of the gripping sleeve, said thickened portion being arranged such that in the attached condition of said cannula on said handpiece, said thickened portion is located below the portion of the cannula containing said passageways for the further advance of the media; said plug connector having an internal hollow space for the receipt of a light-emitting element, and a light-transmissive opening at the end thereof distant from the gripping sleeve for light emitted by said light-emitting element.

2. Spray handpiece as claimed in claim 1 wherein said three passageways comprise, respectively, a middle passageway providing a water channel, and two outer passageways each being an air channel.

3. Spray headpiece as claimed in claim 1, wherein the discharge orifices of said passageways are oriented such that jets of media projected into the surroundings at the free end of said cannula intersect at a point in front of the free end of said cannula.

4. Spray handpiece as claimed in claim 3, wherein the discharge orifice of the middle passageway is directed forwardly from the free end of the cannula, and the discharge orifices of the two outer passageways are directed inwardly towards the axis of the middle discharge orifice.

5. Spray handpiece as claimed in claim 1, wherein said cannula is mounted on said plug connector so as to be rotatable about the axis of the insert opening.

6. Spray handpiece as claimed in claim 1, wherein said passageways in said cannula are slightly inclined relative to the axis of the insert opening.

7. Spray handpiece as claimed in claim 1, wherein said light-emitting element comprises an incandescent lamp and a current supply circuit in the gripping sleeve for powering said lamp.

8. Spray handpiece as claimed in claim 1, wherein a light-conductor is arranged in the light-transmissive opening of the plug connector.

9. Spray handpiece as claimed in claim 1, wherein said plug connector, upon insertion into said insert opening of the cannula, forms transfer chambers in cooperation with the wall structure of said insert opening for transferring the media from the media discharge of said gripping sleeve to radial conduit sections of said passageways.

10. Spray handpiece as claimed in claim 9, wherein said transfer chambers are sealed through sealing rings arranged on said plug connector.

* * * * *